US012714715B2

(12) United States Patent
Inaba et al.

(10) Patent No.: US 12,714,715 B2
(45) Date of Patent: Aug. 25, 2026

(54) AGENT FOR TREATING MYOPIA, PREVENTING MYOPIA AND/OR SUPPRESSING MYOPIA PROGRESSION

(71) Applicants: SANTEN PHARMACEUTICAL CO., LTD., Osaka (JP); BOEHRINGER INGELHEIM INTERNATIONAL GMBH, Ingelheim am Rhein (DE)

(72) Inventors: Takaaki Inaba, Ikoma (JP); Masatomo Kato, Ikoma (JP)

(73) Assignees: SANTEN PHARMACEUTICAL CO., LTD., Osaka (JP); BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 565 days.

(21) Appl. No.: 18/019,395

(22) PCT Filed: Aug. 3, 2021

(86) PCT No.: PCT/JP2021/028770

§ 371 (c)(1),
(2) Date: Feb. 2, 2023

(87) PCT Pub. No.: WO2022/030489

PCT Pub. Date: Feb. 10, 2022

(65) Prior Publication Data

US 2023/0190766 A1 Jun. 22, 2023

(30) Foreign Application Priority Data

Aug. 4, 2020 (JP) ................................. 2020-132626

(51) Int. Cl.

| | |
|---|---|
| ***A61K 31/5513*** | (2006.01) |
| ***A61K 9/00*** | (2006.01) |
| ***A61P 27/06*** | (2006.01) |

(52) U.S. Cl.
CPC ........ *A61K 31/5513* (2013.01); *A61K 9/0048* (2013.01); *A61P 27/06* (2018.01)

(58) Field of Classification Search
None
See application file for complete search history.

(56) References Cited

U.S. PATENT DOCUMENTS

| | | | |
|---|---|---|---|
| 5,716,952 | A | 2/1998 | Woldemussie et al. |
| 2012/0015035 | A1 | 1/2012 | Wildsoet et al. |
| 2021/0267885 | A1 | 9/2021 | Tan et al. |

FOREIGN PATENT DOCUMENTS

| | | | |
|---|---|---|---|
| CN | 109310687 | A | 2/2019 |
| JP | 201821007 | A | 8/2018 |
| WO | 9318772 | A1 | 9/1993 |
| WO | 2018174149 | A1 | 9/2018 |

OTHER PUBLICATIONS

St. Edmund's Eye Hospital, May 21, 2019 (https://stedmundseyehospital.com/11-tips-to-help-you-manage-myopia/). (Year: 2019).*

Barathi et al (Disease Models & Mechanisms, 6, 1146-1158, 2013) (Year: 2013).*

Engel et al (J Med Chem, 1989, 32, 1718-1724) (Year: 1989).*

Barthi et al., "Muscarinic cholinergic receptor (M2) plays a crucial role in the development of myopia in mice", Disease Models & Mechanisms, 2013, vol. 6, pp. 1146-1158.

Engel et al., "Tricyclic compounds as selective muscarinic receptor antagonists. 3. Structure-selectivity relationships in a series of cardioselective (M2) antimuscarinics", J. Med. Chem., 1989, vol. 32, pp. 1718-1724.

International Search Report corresponding to International Application No. PCT/JP2021/028770; Mailing Date, Oct. 5, 2021.

PCT Written Opinion of the International Searching Authority for International Application No. PCT/JP2021/028770; Mailing Date of Oct. 5, 2021.

Lin et al., Muscarinic Acetylcholine Receptor 3 Is Dominant in Myopia Progression; IOVS, Sep. 2012, vol. 53, No. 10; 7 pages.

Zhulenko et al; Textbooks and Teaching Aids For University Students; "Pharmacology", Moscow "KolosS" 2008, pp. 34-35.

* cited by examiner

*Primary Examiner* — Celeste A Roney

(74) *Attorney, Agent, or Firm* — CANTOR COLBURN LLP

(57) ABSTRACT

The present invention relates to a pharmaceutical composition for treating myopia, preventing myopia and/or suppressing myopia progression, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

16 Claims, No Drawings

AGENT FOR TREATING MYOPIA, PREVENTING MYOPIA AND/OR SUPPRESSING MYOPIA PROGRESSION

CROSS REFERENCE TO RELATED APPLICATIONS

This is the U.S. national stage of application No. PCT/JP2021/028770, filed on Aug. 3, 2021. Priority under 35 U.S.C. § 119(a) and 35 U.S.C. § 365(b) is claimed from Japanese Application No. 2020-132626, filed Aug. 4, 2020, the disclosure of which is also incorporated herein by reference.

TECHNICAL FIELD

The present invention relates to an agent for treating myopia, preventing myopia and/or suppressing myopia progression. More specifically, the present invention relates to a pharmaceutical composition for treating myopia, preventing myopia and/or suppressing myopia progression, comprising (+)-11-[2-[2-[(diethylamino)methyl]-1-piperidinyl]acetyl]-5,11-dihydro-6H-pyrido[2,3-b][1,4]benzodiazepin-6-one (hereinafter also referred to as "AFDX0250") or a salt thereof as an active ingredient.

BACKGROUND ART

Myopia is one form of ametropia, which is a pathology that the eyesight blurs because the parallel rays from far distance which enters eyes meets an image in front of the retina. Myopia is considered to be caused by that the image when seeing at a distance is focused not on the retina but in front of the retina in case that the refraction of the cornea or the lens is too strong (refractive myopia) or that the image when seeing at a distance is focused not on the retina but in front of the retina even though the thickness of the lens is reduced in case that the axial length (the length between the cornea and the retina) is extended and is too longer than normal (axial myopia). Also, the onset of myopia at an early age and the rapid myopia progression may lead to high myopia as an adult associated with visually disabling pathologic myopia.

In order to treat myopia, various treatments such as surgery, vision correction with glasses or contact lenses, and treatment with a drug have been carried out. Recently, the treatment with a drug, which is one of myopia treatments, has been actively studied, and some drugs which may be used as an agent for treating myopia have been reported. For example, Patent Literature 1 discloses that atropine (muscarinic antagonist) is useful for the treatment of myopia, and Patent Literature 2 discloses that tiotropium (muscarinic $M_2/M_3$ receptor antagonist), which is used for the treatment of chronic obstructive pulmonary disease (COPD), is effective for preventing myopia, treating myopia and/or suppressing myopia progression. On the other hand, in the treatment of myopia with muscarinic antagonists, there was a problem of significantly reducing or completely preventing the side effects due to mydriatic action. When a person causes mydriasis, the pupil is dilated, and the symptom of glare is induced. The symptom of glare due to the dilation of the pupil may affect the daily life of the person.

Hence, the development of a novel agent for treating myopia, which can prevent the side effects due to mydriatic action, has been strongly desired.

Patent Literature 3 discloses that 11-[2-[2-[(diethylamino)methyl]-1-piperidinyl]acetyl]-5,11-dihydro-6H-pyrido[2,3-b][1,4]benzodiazepin-6-one (hereinafter also referred to as "AFDX0116" or "Otenzepad") is useful for the treatment of glaucoma and/or ocular hypertension and that intraocular pressure is decreased by intracameral injection. Also, it is disclosed that one example of compounds for decreasing intraocular pressure includes AFDX0250 which is dextrorotatory (+)-enantiomer of AFDX0116.

Non-Patent Literature 1 discloses that a selective muscarinic $M_2$ receptor antagonist suppresses myopia progression. Also, it is disclosed that one example of drugs for suppressing myopia progression includes AFDX0116.

However, there is no disclosure that AFDX0250 can be used for treating myopia, preventing myopia and/or suppressing myopia progression. In addition, it has not been reported that ADFX0250 can prevent the side effects due to mydriatic action.

CITATION LIST

Patent Literature

[PL 1] JP 2018-021007
[PL 2] WO 2018/174149
[PL 3] WO 93/18772

Non-Patent Literature

[NPL 1] Dis Model Mech. 2013 September: 6(5): 1146-1158

SUMMARY OF INVENTION

Technical Problem

An object of the present invention is to find a novel compound useful for treating myopia, preventing myopia, and/or suppressing myopia progression. In addition, the object of the present invention is to find an agent for treating myopia which does not substantially have mydriatic action and which is superior in safety and sense of use.

Solution to Problem

The present inventors have intensively studied to reach the aforementioned object, and have focused on (+)-11-[2-[2-[(diethylamino)methyl]-1-piperidinyl]acetyl]-5,11-dihydro-6H-pyrido[2,3-b][1,4]benzodiazepin-6-one (AFDX0250) which has never been used in the study on the treatment of myopia with 11-[2-[2-[(diethylamino)methyl]-1-piperidinyl]acetyl]-5,11-dihydro-6H-pyrido[2,3-b][1,4]benzodiazepin-6-one (AFDX0116) which is selective muscarinic $M_2$ receptor antagonist. The present inventors have found that AFDX0250 suppresses the axial length elongation and the refractive error in an animal model with the symptoms of myopia, and thus is useful for treating myopia, preventing myopia and/or suppressing myopia progression. In addition, the present inventors have found that AFDX0250 not only inhibits mydriatic action produced by the use of muscarinic antagonists to the levels that do not affect daily life but also has a higher margin of safety as compared to any other muscarinic antagonists. Based upon the new findings, the present invention has been completed.

Specifically, the present invention provides the following embodiments.

(1) A pharmaceutical composition for treating myopia, preventing myopia, and/or suppressing myopia progression, comprising (+)-11-[2-[2-[(diethylamino)

methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(2) The pharmaceutical composition of the above (1) which is free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(3) The pharmaceutical composition of the above (1) or (2) which does not substantially have mydriatic action.

(4) The pharmaceutical composition of any one of the above (1) to (3), wherein the myopia is axial myopia, refractive myopia, pseudomyopia, pathological myopia, simple myopia, extreme myopia, severe myopia, high myopia, moderate myopia, low myopia, myopia complicated by glaucoma, myopia at the risk of the onset of glaucoma, or myopia with high intraocular pressure.

(5) The pharmaceutical composition of any one of the above (1) to (4) for ocular topical administration.

(6) The pharmaceutical composition of the above (5), wherein the ocular topical administration is ophthalmic administration, administration by an ophthalmic ointment, conjunctival sac administration, intravitreal administration, subconjunctival administration, sub-Tenon's administration, conjunctival sac injection, or application to the eyelid.

(7) The pharmaceutical composition of any one of the above (1) to (6) which is in the form of an eye drop, an eye gel, an ophthalmic ointment, or an injection.

(8) The pharmaceutical composition of any one of the above (1) to (7), wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.0001-5% (w/v).

(9) The pharmaceutical composition of any one of the above (1) to (7), wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.001-1% (w/v).

(10) The pharmaceutical composition of any one of the above (1) to (7), wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.001% (w/v) or more and less than 1% (w/v).

(11) The pharmaceutical composition of any one of the above (1) to (7), wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.002-0.5% (w/v).

(12) The pharmaceutical composition of any one of the above (1) to (7), wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.002-0.01% (w/v).

(13) The pharmaceutical composition of any one of the above (1) and (3) to (12), wherein the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof is less than 0.1% (w/v).

(14) The pharmaceutical composition of any one of the above (1) and (3) to (13), wherein the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof is 0.05 part by weight or less per part by weight of (+)-11-[2-[2-[(diethylamino)methyl]-1-piperidinyl]acetyl]-5,11-dihydro-6H-pyrido[2,3-b][1,4]benzodiazepin-6-one or a salt thereof.

(15) A pharmaceutical composition for suppressing the axial length elongation, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(16) A pharmaceutical composition for suppressing the refractive error, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(17) Use of (+)-11-[2-[2-[(diethylamino)methyl]-1-piperidinyl]acetyl]-5,11-dihydro-6H-pyrido[2,3-b][1,4]benzodiazepin-6-one or a salt thereof in the manufacture of an agent for treating and/or preventing myopia.

(18) The use of the above (17), wherein the agent is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(19) Use of (+)-11-[2-[2-[(diethylamino)methyl]-1-piperidinyl]acetyl]-5,11-dihydro-6H-pyrido[2,3-b][1,4]benzodiazepin-6-one or a salt thereof in the manufacture of an agent for suppressing myopia progression.

(20) The use of the above (19), wherein the agent is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(21) A method of treating and/or preventing myopia, which comprises administering a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof to a patient.

(22) A method of treating and/or preventing myopia, which comprises administering an agent comprising a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof which is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(23) A method of suppressing myopia progression, which comprises administering a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof to a patient.

(24) A method of suppressing myopia progression, which comprises administering an agent comprising a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof which is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(25) A method of suppressing the axial length elongation, which comprises administering a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof to a patient.

(26) A method of suppressing the axial length elongation, which comprises administering an agent comprising a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof which is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(27) A method of suppressing the refractive error, which comprises administering a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof to a patient.

(28) A method of suppressing the refractive error, which comprises administering an agent comprising a therapeutically effective amount of (+)-11-[2-[2-[(diethylamino)methyl]-1-piperidinyl]acetyl]-5,11-dihydro-6H-pyrido[2,3-b][1,4]benzodiazepin-6-one or a salt thereof which is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

(29) (+)-11-[2-[2-[(Diethylamino)methyl]-1-piperidinyl]acetyl]-5,11-dihydro-6H-pyrido[2,3-b][1,4]benzodiazepin-6-one or a salt thereof for the use in treating and/or preventing myopia.

(30) (+)-11-[2-[2-[(Diethylamino)methyl]-1-piperidinyl]acetyl]-5,11-dihydro-6H-pyrido[2,3-b][1,4]benzodiazepin-6-one or a salt thereof for the use in suppressing myopia progression.

Each feature of the above (1) to (30) can be optionally selected and combined two or more.

Advantageous Effects of Invention

According to the present invention, the pharmaceutical composition comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, which not only produces effects for treating myopia, preventing myopia and/or suppressing myopia progression but also prevents mydriatic action produced by the use of muscarinic antagonists to the levels that do not affect daily life, can be provided. In addition, (+)-11-[2-[2-[(diethylamino)methyl]-1-piperidinyl]acetyl]-5,11-dihydro-6H-pyrido[2,3-b][1,4]benzodiazepin-6-one does not substantially have mydriatic action and has a high margin of safety, and thus the pharmaceutical composition of the present invention is expected to be used as an agent for treating myopia which is superior in safety and sense of use.

DESCRIPTION OF EMBODIMENTS

Hereinafter, the present invention is explained in detail.

As used herein, "(+)-11-[2-[2-[(diethylamino)methyl]-1-piperidinyl]acetyl]-5,11-dihydro-6H-pyrido[2,3-b][1,4]benzodiazepin-6-one" or "AFDX0250" is a compound of the following formula (CAS Registration No. 121029-35-4):

[Chem. 1]

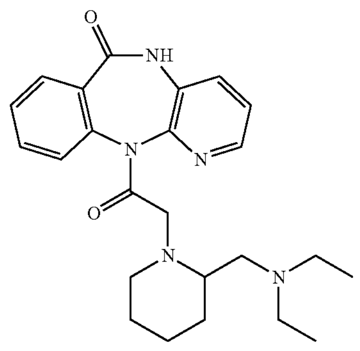

In the present invention, (+)-11-[2-[2-[(diethylamino)methyl]-1-piperidinyl]acetyl]-5,11-dihydro-6H-pyrido[2,3-b][1,4]benzodiazepin-6-one may be in a salt form, and it is not particularly limited as long as the salt is a pharmaceutically acceptable salt. Examples thereof include a salt with an inorganic acid such as hydrochloric acid, hydrobromic acid, hydroiodic acid, nitric acid, sulfuric acid and phosphoric acid; a salt with an organic acid such as acetic acid, oxalic acid, fumaric acid, maleic acid, succinic acid, malic acid, citric acid, tartaric acid, adipic acid, gluconic acid, glucoheptonic acid, glucuronic acid, terephthalic acid, methanesulfonic acid, alanine, lactic acid, hippuric acid, 1,2-ethanedisulfonic acid, isethionic acid, lactobionic acid, oleic acid, gallic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid and sulfosalicylic acid; a salt with a metal such as sodium, potassium, calcium and magnesium; a salt with an inorganic compound such as ammonia; and a salt with an organic amine such as triethylamine and guanidine.

In the pharmaceutical composition of the present invention, (+)-11-[2-[2-[(diethylamino)methyl]-1-piperidinyl]acetyl]-5,11-dihydro-6H-pyrido[2,3-b][1,4]benzodiazepin-6-one or a salt thereof may be in the form of a hydrate or a solvate.

In the present invention, (+)-11-[2-[2-[(diethylamino)methyl]-1-piperidinyl]acetyl]-5,11-dihydro-6H-pyrido[2,3-b][1,4]benzodiazepin-6-one or a salt thereof may be prepared according to a well-known method in the organic chemistry field or may be also obtained as a commercially available product. For example, (+)-11-[2-[2-[(diethylamino)methyl]-1-piperidinyl]acetyl]-5,11-dihydro-6H-pyrido[2,3-b][1,4]benzodiazepin-6-one can be prepared according to the step described in J. Med. Chem., 32(8), 1718-24, 1989.

The concentration of (+)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition of the present invention is not particularly limited, but it is preferably a concentration that the axial length elongation and/or the refractive error is/are suppressed when topically administering to the patient's eyes. The lower limit thereof is preferably 0.0001% (w/v), more preferably 0.0003% (w/v), furthermore preferably 0.0005% (w/v), even more preferably 0.001% (w/v), particularly 0.0013% (w/v), particularly more preferably 0.0015% (w/v), particularly furthermore preferably 0.0017% (w/v), and most preferably 0.002% (w/v). In addition, the concentration is preferably a concentration that the mydriatic action is not caused when topically administering to the patient's eyes. Hence, the upper limit thereof is preferably 5% (w/v), more preferably 3% (w/v), furthermore preferably 2% (w/v), even more preferably 1% (w/v), particularly preferably 0.5% (w/v), particularly more preferably 0.1% (w/v), particularly furthermore preferably 0.02% (w/v), particularly even more preferably 0.01% (w/v), and most preferably 0.004% (w/v). Also, the upper limit thereof is preferably the same concentration as the minimum concentration that the mydriatic action is not caused when topically administering to the patient's eyes, more preferably ½ of the minimum concentration, furthermore preferably ⅕ of the minimum concentration, even more preferably 1/10 of the minimum concentration, particularly preferably 1/50 of the minimum concentration, and most preferably 1/100 of the minimum concentration. The range of the concentration that the axial length elongation and/or the refractive error is/are suppressed when topically administering to the patient's eyes as well as the concentration that the mydriatic action is not caused when topically administering to the patient's eyes is preferably 0.001-1% (w/v) or 0.001% (w/v) or more and less than 1% (w/v), more preferably 0.002-0.5% (w/v), furthermore preferably 0.002-0.1% (w/v), even more preferably 0.002-0.02% (w/v), particularly preferably 0.002-0.01% (w/v), particularly more preferably 0.0015-0.02% (w/v), particularly furthermore preferably 0.0017-0.01% (w/v), and most preferably 0.002-0.004% (w/v). The concentration of the compound in an eye drop is, for example, preferably 0.0001-5% (w/v), more preferably 0.0003-2% (w/v), furthermore preferably 0.0005-1% (w/v), even more preferably 0.001-0.5% (w/v), particularly preferably 0.0013-0.1% (w/v), particularly more preferably 0.0015-0.02% (w/v), particularly furthermore preferably 0.0017-0.01% (w/v), and most preferably 0.002-0.004% (w/v). The concentration of the compound in an ophthalmic ointment is, for example, preferably 0.0001-5% (w/w) and more preferably 0.001-3% (w/w).

As used herein, the term "% (w/v)" means the mass (g) of an object ingredient in 100 mL of the pharmaceutical composition of the present invention, and the term "% (w/w)" means the mass (g) of an object ingredient in 100 g of the pharmaceutical composition of the present invention. When the pharmaceutical composition of the present invention comprises a salt of (+)-11-[2-[2-[(diethylamino)methyl]-1-piperidinyl]acetyl]-5,11-dihydro-6H-pyrido[2,3-b][1,4]benzodiazepin-6-one, the values may mean the concentration of the salt of (+)-11-[2-[2-[(diethylamino)methyl]-1-piperidinyl]acetyl]-5,11-dihydro-6H-pyrido[2,3-b][1,4]benzodiazepin-6-one or the concentration of (+)-11-[2-[2-[(diethylamino)methyl]-1-piperidinyl]acetyl]-5,11-dihydro-6H-pyrido[2,3-b][1,4]benzodiazepin-6-one. In addition, when the pharmaceutical composition of the present invention comprises (+)-11-[2-[2-[(diethylamino)methyl]-1-piperidinyl]acetyl]-5,11-dihydro-6H-pyrido[2,3-b][1,4]benzodiazepin-6-one or a salt thereof in the form of a hydrate or a solvate, the values may mean the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof in the form of a hydrate or a solvate or the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof. Hereinafter, the same shall apply to the followings unless otherwise specified.

As used herein, the term "substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof" means that the pharmaceutical composition comprises none of (−)-11-[2-[2-[(diethylamino)methyl]-1-piperidinyl]acetyl]-5,11-dihydro-6H-pyrido[2,3-b][1,4]benzodiazepin-6-one or a salt thereof, that (−)-11-[2-[2-[(diethylamino)methyl]-1-piperidinyl]acetyl]-5,11-dihydro-6H-pyrido[2,3-b][1,4]benzodiazepin-6-one or a salt thereof is not detected by a commonly-used method in pharmaceutical analysis such as liquid column chromatography by chiral column (Detector: UV absorption photometer), that the pharmaceutical composition comprises (−)-11-[2-[2-[(diethylamino)methyl]-1-piperidinyl]acetyl]-5,11-dihydro-6H-pyrido[2,3-b][1,4]benzodiazepin-6-one or a salt thereof in such a concentration that does not produce its own effects and side effects by itself, or that the pharmaceutical composition comprises (−)-11-[2-[2-[(diethylamino)methyl]-1-piperidinyl]acetyl]-5,11-dihydro-6H-pyrido[2,3-b][1,4]benzodiazepin-6-one in such a concentration that is inevitably mixed as an impurity in manufacturing. For example, the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition is less than 0.1% (w/v), preferably 0.05% (w/v) or less, more preferably 0.001% (w/v) or less, furthermore preferably 0.0005% (w/v) or less, even more preferably 0.0001% (w/v) or less, particularly preferably 0.00005% (w/v) or less and most preferably 0.00001% (w/v) or less. Also, the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition is preferably 0.05 part by weight or less, more preferably 0.03 part by weight or less, furthermore preferably 0.02 part by weight or less, even more preferably 0.01 part by weight, particularly preferably 0.005 part by weight, and most preferably 0.001 part by weight per part by weight of (+)-11-[2-[2-[(diethylamino)methyl]-1-piperidinyl]acetyl]-5,11-dihydro-6H-pyrido[2,3-b][1,4]benzodiazepin-6-one or a salt thereof. The concentration of (−)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition is preferably as low as possible from the viewpoint of the effect, while the compound may be inevitably mixed as an impurity in the manufacture of any manufacturing methods. In view of such situation, it is found that the lower limit of the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition is 0.000005% (w/v), preferably 0.000001% (w/v) based on the total pharmaceutical composition or is 0.0005 part by weight and preferably 0.0001 part by weight per part by weight of (+)-11-[2-[2-[(diethylamino)methyl]-1-piperidinyl]acetyl]-5,11-dihydro-6H-pyrido[2,3-b][1,4]benzodiazepin-6-one or a salt thereof in the pharmaceutical composition.

As used herein, the term "myopia" is defined as a refractive state of an uncorrected eye where parallel rays meet the eye in front of the retina. The "myopia" used herein includes all and every known classification and definition of myopia including, for example, axial myopia, refractive myopia, pseudomyopia, pathological myopia, simple myopia, extreme myopia, severe myopia, high myopia, moderate myopia, low myopia, myopia complicated by glaucoma (particularly, juvenile glaucoma), myopia at the risk of the onset of glaucoma, and myopia with high intraocular pressure, preferably axial myopia, extreme myopia, severe myopia, high myopia, and myopia complicated by glaucoma (particularly, juvenile glaucoma), and more preferably axial myopia.

As used herein, the term "treatment (treating)" means every treatment of myopia or the associated symptoms, for example, treating or improving myopia, particularly axial myopia and/or refractive myopia and alleviating or inhibiting symptoms associated with myopia. The treatment also encompasses inhibiting recurrence of myopia.

As used herein, the term "prophylaxis (preventing)" means preventing the onset of myopia, delaying the onset of myopia, or reducing the risk of the onset of myopia.

As used herein, the term "suppression of myopia progression (suppressing myopia progression)" means delaying the myopia progression (delay of myopia progression) or reducing the myopia progression (reduction of myopia progression).

Also, the term "treating myopia, preventing myopia and/or suppressing myopia progression" used herein includes suppressing the axial length elongation and/or suppressing the refractive error.

As used herein, the term "not substantially have mydriatic action" means that the pharmaceutical composition does not have mydriatic action at the level that affects daily life. The term includes that the pharmaceutical composition has no mydriatic action. In addition, even if mydriatic action is found in any measuring way, it is interpreted as "not substantially have mydriatic action" when the treated patient does not experience visual side effects of glare and pupil dilation which affect daily life.

The pharmaceutical composition of the present invention has a high margin of safety and may have higher safety as compared to an agent for treating myopia comprising other muscarinic receptor antagonist. As used herein, the term "margin of safety" means the range between the minimum effective concentration for producing the therapeutic effect of myopia and the maximum effective concentration for producing the therapeutic effect without mydriatic action. The margin of safety of the present invention is calculated according to maximum effective concentration/minimum effective concentration, and is, for example, 10 or more, preferably 100 or more, more preferably 150 or more, furthermore preferably 200 or more, and even more preferably 250 or more.

The pharmaceutical composition of the present invention can be widely used regardless of the patient's age. In addition, the pharmaceutical composition can be used for preventing myopia in schoolage children or in teenagers or adults with myopia progression, and/or suppressing myopia progression in schoolage children or in teenagers or adults with myopia progression.

As used herein, the term "patient" means human and an animal such as dog, cat, and house. Among them, the patient is preferably human.

As used herein, the term "therapeutically effective amount" means a concentration for producing the therapeutic effect of myopia and the associated symptoms or a concentration for delaying the onset or progression of myopia, relative to untreated subjects.

The pharmaceutical composition of the present invention may comprise a pharmaceutically acceptable active ingredient other than (+)-11-[2-[2-[(diethylamino)methyl]-1-piperidinyl]acetyl]-5,11-dihydro-6H-pyrido[2,3-b][1,4]benzodiazepin-6-one or a salt thereof unless otherwise noted.

The pharmaceutical composition of the present invention may be administered orally or parenterally. Examples of the administration route include oral administration, intravenous administration, transdermal administration, and ocular topical administration (e.g., ophthalmic administration, administration by an ophthalmic ointment, conjunctival sac administration, intravitreal administration, subconjunctival administration, sub-Tenon's administration, conjunctival sac injection, application to the eyelid).

The pharmaceutical composition of the present invention can be prepared with an active ingredient and one or more pharmaceutically acceptable additives in a desired dosage form such as an oral agent such as a tablet, a capsule, a granule, a powder, a lozenge, a syrup, an emulsion and a suspension or a parenteral agent such as an eye drop, an eye gel, an ophthalmic ointment, an injection, a suppository and a nasal agent according to a commonly-used method in the art. The preferred dosage form of the pharmaceutical composition of the present invention includes an eye drop, an eye gel, an ophthalmic ointment and an injection.

When the pharmaceutical composition of the present invention is prepared as an eye drop, the eye drop can be prepared by adding an active ingredient to a medium such as purified water and a buffer and stirring, and then adjusting the pH of the mixture with a pH adjuster.

Also, as appropriate, a commonly-used additive may be added into an eye drop. Examples thereof include a tonicity agent, a buffering agent, a surfactant, a stabilizing agent, a preservative, a solubilizing agent, or the like.

When the pharmaceutical composition of the present invention is prepared as an eye drop, the pH of the eye drop is not limited as long as the pH is in an acceptable range for ophthalmic formulations.

When the pharmaceutical composition of the present invention is prepared as an ophthalmic ointment, a commonly-used base material may be used therein. Examples of the base material include white petrolatum, liquid paraffin, or the like.

The oral agent such as a tablet, a capsule, a granule, and a powder can be prepared with an additive such as an extending agent, a lubricant, a binder, a disintegrant, a coating agent and a film coating agent, as appropriate. Examples of the extending agent include lactose, crystalline cellulose, starch and vegetable oil, examples of the lubricant include magnesium stearate and talc, examples of the binder include hydroxypropylcellulose and polyvinylpyrrolidone, examples of the disintegrant include carboxymethylcellulose calcium and low substituted hydroxypropylcellulose, examples of the coating agent include hydroxypropylmethylcellulose, macrogol (polyethyleneglycol) and silicone resin, and examples of the film coating agent include gelatin film.

The dose and administration of the pharmaceutical composition of the present invention can be suitably changed depending on various conditions such as dosage form, symptom, age and weight of a patient, age at the onset of myopia, and doctor's discretion. For example, when the pharmaceutical composition of the present invention is used for ocular topical administration as an eye drop, the dose and administration thereof is not particularly limited as long as it is sufficient to exhibit a desired efficacy. The eye drop can be administered at a dose of 1 drop to several drops a time, 1 to several times daily (e.g., 1 to 4 times, 1 to 6 times, or 1 to 8 times). Also, the eye drop can be used with wearing contact lenses.

EXAMPLES

Hereinafter, the present invention is illustrated in Examples in order to make it easy to understand the present invention. The present invention, however, is not intended to be limited thereto by any means.

Example 1: Test on Suppression of Myopia Progression (Axial Length Elongation and Refractive Error) in Guinea Pig Myopia Model (1)

According to the following procedures, the effect of AFDX0250 on the suppression of myopia progression (the axial length elongation and the refractive error) was evaluated.

(Preparation of Sample)

AFDX0250 was dissolved in purified water with a buffering agent and a tonicity agent to prepare 0.5% AFDX0250 solution. 1 mol/L sodium hydroxide reagent solution or dilute hydrochloric acid was added to the solution to adjust the pH thereof to neutral. Also, a buffering agent and a tonicity agent were dissolved in purified water to prepare a neutral vehicle. 9.8 mL of the vehicle was mixed with 0.2 mL of 0.5% AFDX0250 solution and stirred to prepare 0.01% AFDX0250 solution. 3 mL, 4 mL and 4.5 mL of the vehicles were mixed with 2 mL, 1 mL and 0.5 mL of 0.01% AFDX0250 solutions, respectively, and stirred to prepare 0.004%, 0.002% and 0.001% AFDX0250 solutions.

(Preparation of Guinea Pig Myopia Model)

A test tube with a diameter of 18 mm was cut off at the level of 10 mm from the bottom, and the cut-off bottom part was glued to one side of Velcro tape (about 20 mm square) with a hole of an appropriate diameter in the center with an adhesive agent to prepare a lens (goggle). 3-week-old guinea pigs (Slc:Hartley) (n=30) were obtained, and the prepared goggle was covered to the right eye of each guinea pig with an adhesive agent to induce myopia to the guinea pigs. The left eye thereof without goggle was used as control.

(Administration of Sample)

The prepared guinea pig myopia models were randomly classified into 0.001% AFDX0250 solution administration group, 0.002% AFDX0250 solution administration group, 0.004% AFDX0250 solution administration group, 0.01% AFDX0250 solution administration group and vehicle administration group (control group) (n=6 per group). In the AFDX0250 solution administration groups, 10 μL of the AFDX0250 solution in each concentration was topically administered to the right eye of each guinea pig once daily for 14 days from the day when the right eye was covered with the goggle (day 0) to day 13. In the control group, 10 μL of the vehicle was topically administered to the right eye of each guinea pig once daily for 14 days from the day when the right eye was covered with the goggle (day 0) to day 13. In the all groups, 10 μL of the vehicle was topically administered to the left eye at the same frequency of administration as that of each group daily for 14 days from day 0 to day 13. The guinea pigs were reared under a normal rearing condition.

TABLE 1

| Test group | n | Treatment with goggle | | Sample | Administration route (10 μL/eye) | Frequency of administration (/day) |
|---|---|---|---|---|---|---|
| vehicle administration group | 6 | right eye | + | vehicle | Topical administration | Once |
| | | left eye | − | vehicle | | |
| 0.001% AFDX0250 solution administration group | 6 | right eye | + | 0.001% AFDX0250 solution | Topical administration | Once |
| | | left eye | − | vehicle | | |
| 0.002% AFDX0250 solution administration group | 6 | right eye | + | 0.002% AFDX0250 solution | Topical administration | Once |
| | | left eye | − | vehicle | | |
| 0.004% AFDX0250 solution administration group | 6 | right eye | + | 0.004% AFDX0250 solution | Topical administration | Once |
| | | left eye | − | vehicle | | |
| 0.01% AFDX0250 solution administration group | 6 | right eye | + | 0.01% AFDX0250 solution | Topical administration | Once |
| | | left eye | − | Vehicle | | |

(Evaluation Method)

On day 14 from the myopia induction, the axial lengths of right and left eyeballs were measured with an ultrasound axial length measurement device ECHOSCAN US-500 (A-scan) (NIDEK CO., LTD.), and the refractions were measured with the auto refractometer AR-1a (NIDEK CO., LTD.). The difference of axial lengths and the suppression rate of the axial length elongation as well as the difference of refraction and the suppression rate of the refractive error were calculated according to the following formulae. The calculation was performed in Microsoft Excel.

Difference of axial lengths (mm)=Axial length of right eye (mm)−Axial length of left eye (mm)

Suppression rate of axial length elongation (%)=(1−Difference of axial lengths in AFDX0250 solution administration group/Difference of axial lengths in control group)×100 (Formula)

Difference of refraction (*D*)=Refraction of right eye (*D*)−Refraction of left eye (*D*)

Suppression rate of refractive error (%)=(1−Difference of refraction in AFDX0250 solution administration group/Difference of refraction in control group)×100 (Formula)

(Test Result)

The average values of the difference of axial lengths and the difference of refraction in the control group and in each AFDX0250 solution administration group are shown in Table 2.

TABLE 2

| | Difference of axial lengths (mm) | Difference of refraction (D) |
|---|---|---|
| vehicle administration group | 0.20 | −7.92 |
| 0.001% AFDX0250 solution administration group | 0.17 | −6.12 |
| 0.002% AFDX0250 solution administration group | 0.09 | −2.78 |
| 0.004% AFDX0250 solution administration group | 0.07 | −2.39 |
| 0.01% AFDX0250 solution administration group | 0.06 | −3.63 |

The suppression rate of the axial length elongation and the suppression rate of the refractive error in each AFDX0250 solution administration group are shown in Table 3. The suppression rates were calculated using the values before rounding off to the values in Table 2, respectively.

TABLE 3

| | Suppression rate of axial length elongation (%) | Suppression rate of refraction (%) |
|---|---|---|
| 0.001% AFDX0250 solution administration group | 15.85 | 22.78 |
| 0.002% AFDX0250 solution administration group | 55.46 | 64.95 |
| 0.004% AFDX0250 solution administration group | 63.39 | 69.80 |
| 0.01% AFDX0250 solution administration group | 68.58 | 54.19 |

Example 2: Test on Suppression of Myopia Progression (Axial Length Elongation and Refractive Error) in Guinea Pig Myopia Model (2)

According to the following procedures, the effect of AFDX0250 on the suppression of myopia progression (the axial length elongation and the refractive error) was evaluated.

(Preparation of Sample)

AFDX0250 was dissolved in purified water with a buffering agent and a tonicity agent to prepare 0.5% AFDX0250 solution. 1 mol/L sodium hydroxide reagent solution or dilute hydrochloric acid was added to the solution to adjust the pH thereof to neutral. Also, a buffering agent and a tonicity agent were dissolved in purified water to prepare a neutral vehicle. 4 mL and 4.8 mL of vehicles were mixed with 1 mL and 0.2 mL of 0.5% AFDX0250 solutions, respectively, and stirred to prepare 0.1% and 0.02% of AFDX0250 solutions. Also, 4 mL of the vehicle was mixed with 1 mL of 0.02% AFDX0250 solution and stirred to prepare 0.004% AFDX0250 solution.

(Preparation of Guinea Pig Myopia Model)

Guinea pig myopia models (n=30) were prepared according to similar method to that of (Preparation of guinea pig myopia model) of Example 1.

(Administration of Sample)

The prepared guinea pig myopia models were randomly classified into 0.004% AFDX0250 solution administration group, 0.02% AFDX0250 solution administration group, 0.1% AFDX0250 solution administration group, 0.5% AFDX0250 solution administration group and vehicle administration group (control group) (n=6 per group). In the AFDX0250 solution administration groups, 10 μL of the AFDX0250 solution in each concentration was topically administered to the right eye of each guinea pig once daily for 14 days from the day when the right eye was covered with the goggle (day 0) to day 13. In the control group, 10 μL of the vehicle was topically administered to the right eye of each guinea pig once daily for 14 days from day 0 to day 13. In the all groups, 10 μL of the vehicle was topically administered to the left eye at the same frequency of administration as that of each group daily for 14 days from day 0 to day 13. The guinea pigs were reared under a normal rearing condition.

TABLE 4

| Test group | n | Treatment with goggle | | Sample | Administration route (10 μL/eye) | Frequency of administration (/day) |
|---|---|---|---|---|---|---|
| vehicle administration group | 6 | right eye | + | vehicle | Topical administration | Once |
| | | left eye | − | vehicle | | |
| 0.004% AFDX0250 solution administration group | 6 | right eye | + | 0.004% AFDX0250 solution | Topical administration | Once |
| | | left eye | − | vehicle | | |
| 0.02% AFDX0250 solution administration group | 6 | right eye | + | 0.02% AFDX0250 solution | Topical administration | Once |
| | | left eye | − | vehicle | | |
| 0.1% AFDX0250 solution administration group | 6 | right eye | + | 0.1% AFDX0250 solution | Topical administration | Once |
| | | left eye | − | Vehicle | | |
| 0.5% AFDX0250 solution administration group | 6 | right eye | + | 0.5% AFDX0250 solution | Topical administration | Once |
| | | left eye | − | Vehicle | | |

(Evaluation Method)

The axial lengths and the refraction of right and left eyes were measured according to similar method to that of (Evaluation method) of Example 1, and the difference of axial lengths and the suppression rate of the axial length elongation as well as the difference of refraction and the suppression rate of the refractive error were calculated according to the formulae shown in Example 1. The calculation was performed in Microsoft Excel.

(Test Result)

The average values of the difference of axial lengths and the difference of refraction in the control group and in each AFDX0250 solution administration group are shown in Table 5.

TABLE 5

| | Difference of axial lengths (mm) | Difference of refraction (D) |
|---|---|---|
| vehicle administration group | 0.20 | −7.99 |
| 0.004% AFDX0250 solution administration group | 0.07 | −3.25 |
| 0.02% AFDX0250 solution administration group | 0.05 | −2.52 |
| 0.1% AFDX0250 solution administration group | 0.04 | −2.05 |
| 0.5% AFDX0250 solution administration group | 0.02 | −2.03 |

The suppression rate of the axial length elongation and the suppression rate of the refractive error in each AFDX0250 solution administration group are shown in Table 6. The suppression rates were calculated using the values before rounding off to the values in Table 5, respectively.

TABLE 6

| | Suppression rate of axial length elongation (%) | Suppression rate of refractive error (%) |
|---|---|---|
| 0.004% AFDX0250 solution administration group | 66.85 | 59.27 |
| 0.02% AFDX0250 solution administration group | 74.16 | 68.43 |
| 0.1% AFDX0250 solution administration group | 79.21 | 74.35 |
| 0.5% AFDX0250 solution administration group | 88.48 | 74.64 |

As clearly exhibited in the results of Examples 1 and 2, AFDX0250 strongly suppressed the axial length elongation and the refractive error. As a result, it was shown that AFDX0250 was effective for treating myopia, preventing myopia and/or suppressing myopia progression.

Comparative Example 1: Test on Suppression of Myopia Progression (Axial Length Elongation and Refractive Error) in Guinea Pig Myopia Model (1)

According to the following procedures, the effect of AFDX0116 on the suppression of myopia progression (the axial length elongation and the refractive error) was evaluated.

(Preparation of Sample)

AFDX0116 was dissolved in purified water with a buffering agent and a tonicity agent to prepare 0.5% AFDX0116 solution. 1 mol/L sodium hydroxide reagent solution or dilute hydrochloric acid was added to the solution to adjust the pH thereof to neutral. Also, a buffering agent and a tonicity agent were dissolved in purified water to prepare a neutral vehicle. 4 mL and 4.8 mL of the vehicles were mixed with 1 mL and 0.2 mL of 0.5% AFDX0116 solutions, respectively, and stirred to prepare 0.1% and 0.02% of AFDX0116 solutions. Also, 4 mL of the vehicle was mixed with 1 mL of 0.02% AFDX0116 solution and stirred to prepare 0.004% AFDX0116 solution.

(Preparation of Myopia Guinea Pig Model)

Guinea pig myopia models (n=30) were prepared according to similar method to that of (Preparation of guinea pig myopia model) in Example 1.

(Administration of Sample)

The prepared guinea pig myopia models were randomly classified into 0.004% AFDX0116 solution administration group, 0.02% AFDX0116 solution administration group, 0.1% AFDX0116 solution administration group, 0.5% AFDX0116 solution administration group and vehicle administration group (control group) (n=6 per group). In the AFDX0116 solution administration groups, 10 μL of the AFDX0116 solution in each concentration was topically administered to the right eye of each guinea pig once daily for 14 days from the day when the right eye was covered with the goggle (day 0) to day 13. In the control group, 10 μL of the vehicle was topically administered to the right eye of each guinea pig once daily for 14 days from day 0 to day 13. In the all groups, 10 μL of the vehicle was topically administered to the left eye at the same frequency of administration as that of each group daily for 14 days from day 0 to day 13. The guinea pigs were reared under a normal rearing condition.

TABLE 7

| Test group | n | | Treatment with goggle | Sample | Administration route (10 μL/eye) | Frequency of administration (/day) |
|---|---|---|---|---|---|---|
| vehicle administration group | 6 | right eye | + | vehicle | Topical administration | Once |
| | | left eye | − | vehicle | | |
| 0.004% AFDX0116 solution administration group | 6 | right eye | + | 0.004% AFDX0116 solution | Topical administration | Once |
| | | left eye | − | vehicle | | |
| 0.02% AFDX0116 solution administration group | 6 | right eye | + | 0.02% AFDX0116 solution | Topical administration | Once |
| | | left eye | − | vehicle | | |
| 0.1% AFDX0116 | 6 | right | + | 0.1% AFDX0116 | Topical | Once |

TABLE 7-continued

| Test group | n | Treatment with goggle | | Sample | Administration route (10 µL/eye) | Frequency of administration (/day) |
|---|---|---|---|---|---|---|
| solution administration group | | eye left eye | − | solution vehicle | administration | |
| 0.5% AFDX0116 solution administration group | 6 | right eye left eye | + − | 0.5% AFDX0116 solution vehicle | Topical administration | Once |

(Evaluation Method)

The axial lengths and the refraction of right and left eyes were measured according to similar method to that of (Evaluation method) of Example 1, and the difference of axial lengths and the suppression rate of the axial length elongation as well as the difference of refraction and the suppression rate of the refractive error were calculated according to the formulae shown in Example 1. The calculation was performed in Microsoft Excel.

(Test Result)

The average values of the difference of axial lengths and the difference of refraction in the control group and in each AFDX0116 solution administration group are shown in Table 8.

TABLE 8

| | Difference of axial lengths (mm) | Difference of refraction (D) |
|---|---|---|
| vehicle administration group | 0.24 | −8.70 |
| 0.004% AFDX0116 solution administration group | 0.19 | −4.74 |
| 0.02% AFDX0116 solution administration group | 0.09 | −2.17 |
| 0.1% AFDX0116 solution administration group | 0.09 | −1.90 |
| 0.5% AFDX0116 solution administration group | 0.03 | −2.10 |

The suppression rate of the axial length elongation and the suppression rate of the refractive error in each AFDX0116 solution administration group are shown in Table 9. The suppression rates were calculated using the values before rounding off to the values in Table 8, respectively.

TABLE 9

| | Suppression rate of axial length elongation (%) | Suppression rate of refractive error (%) |
|---|---|---|
| 0.004% AFDX0116 solution administration group | 21.14 | 45.54 |
| 0.02% AFDX0116 solution administration group | 62.95 | 73.10 |
| 0.1% AFDX0116 solution administration group | 63.86 | 73.17 |

TABLE 9-continued

| | Suppression rate of axial length elongation (%) | Suppression rate of refractive error (%) |
|---|---|---|
| 0.5% AFDX0116 solution administration group | 87.73 | 75.86 |

Comparative Example 2: Test on Suppression of Myopia Progression (Axial Length Elongation and Refractive Error) in Guinea Pig Myopia Model (2)

According to the following procedures, the effect of AFDX0116 on the suppression of myopia progression (the axial length elongation and the refractive error) was evaluated.

(Preparation of Sample)

AFDX0116 was dissolved in purified water with a buffering agent and a tonicity agent to prepare 0.5% AFDX0116 solution. 1 mol/L sodium hydroxide reagent solution or dilute hydrochloric acid was added to the solution to adjust the pH thereof to neutral. Also, a buffering agent and a tonicity agent were dissolved in purified water to prepare a neutral vehicle. 4 mL and 4.8 mL of the vehicles were mixed with 1 mL and 0.2 mL of 0.5% AFDX0116 solutions, respectively, and stirred to prepare 0.1% and 0.02% of AFDX0116 solutions. Also, 2.5 mL and 4 mL of the vehicles were mixed with 2.5 mL and 1 mL of 0.02% AFDX0116 solutions, respectively, and stirred to prepare 0.01% and 0.004% AFDX0116 solutions.

(Preparation of Guinea Pig Myopia Model)

Guinea pig myopia models (n=30) were prepared according to similar method to that of (Preparation of guinea pig myopia model) in Example 1.

(Administration of Sample)

The prepared guinea pig myopia models were randomly classified into 0.004% AFDX0116 solution administration group, 0.01% AFDX0116 solution administration group, 0.02% AFDX0116 solution administration group, 0.1% AFDX0116 solution administration group and vehicle administration group (control group) (n=6 per group). In the AFDX0116 solution administration groups, 10 µL of the AFDX0116 solution in each concentration was topically administered to the right eye of each guinea pig once daily for 14 days from the day when the right eye was covered with the goggle (day 0) to day 13. In the control group, 10 µL of the vehicle was topically administered to the right eye of each guinea pig once daily for 14 days from day 0 to day 13. In the all groups, 10 µL of the vehicle was topically administered to the left eye at the same frequency of administration as that of each group daily for 14 days from day 0 to day 13. The guinea pigs were reared under a normal rearing condition.

TABLE 10

| Test group | n | Treatment with goggle | | Sample | Administration route (10 μL/eye) | Frequency of administration (/day) |
|---|---|---|---|---|---|---|
| vehicle administration group | 6 | right eye | + | vehicle | Topical administration | Once |
| | | left eye | − | vehicle | | |
| 0.004% AFDX0116 solution administration group | 6 | right eye | + | 0.004% AFDX0116 solution | Topical administration | Once |
| | | left eye | − | vehicle | | |
| 0.01% AFDX0116 solution administration group | 6 | right eye | + | 0.01% AFDX0116 solution | Topical administration | Once |
| | | left eye | − | vehicle | | |
| 0.02% AFDX0116 solution administration group | 6 | right eye | + | 0.02% AFDX0116 solution | Topical administration | Once |
| | | left eye | − | vehicle | | |
| 0.1% AFDX0116 solution administration group | 6 | right eye | + | 0.1% AFDX0116 solution | Topical administration | Once |
| | | left eye | − | vehicle | | |

(Evaluation Method)

The axial lengths and the refraction of right and left eyes were measured according to similar method to that of (Evaluation Method) of Example 1, and the difference of axial lengths and the suppression rate of the axial length elongation as well as the difference of refraction and the suppression rate of the refractive error were calculated according to the formulae shown in Example 1. The calculation was performed in Microsoft Excel.

(Test Result)

The average values of the difference of axial lengths and the difference of refraction in the control group and in each AFDX0116 solution administration group are shown in Table 11.

TABLE 11

| | Difference of axial lengths (mm) | Difference of refraction (D) |
|---|---|---|
| vehicle administration group | 0.15 | −7.32 |
| 0.004% AFDX0116 solution administration group | 0.12 | −6.59 |
| 0.01% AFDX0116 solution administration group | 0.12 | −3.61 |
| 0.02% AFDX0116 solution administration group | 0.05 | −2.52 |
| 0.1% AFDX0116 solution administration group | 0.05 | −2.42 |

The suppression rate of the axial length elongation and the suppression rate of the refractive error in each AFDX0116 solution administration group are shown in Table 12. The suppression rates were calculated using the values before rounding off to the values in Table 11, respectively.

TABLE 12

| | Suppression rate of axial length elongation (%) | Suppression rate of refractive error (%) |
|---|---|---|
| 0.004% AFDX0116 solution administration group | 22.52 | 9.96 |
| 0.01% AFDX0116 solution administration group | 21.44 | 50.71 |
| 0.02% AFDX0116 solution administration group | 69.73 | 65.61 |
| 0.1% AFDX0116 solution administration group | 68.65 | 66.87 |

As clearly exhibited in the results of Comparative Examples 1 and 2, AFDX0116 suppressed the axial length elongation and the refractive error. As a result, it was demonstrated that the concentration of AFDX0116 showing the anti-myopic effect was higher than that of AFDX0250.

Example 3. Evaluation of Mydriatic Action in AFDX0116 and AFDX0250 Solutions

AFDX0116 and AFDX0250 solutions were repeatedly topically administered to one eye of guinea pigs, respectively, to evaluate the effect of each solution on mydriasis.

(Preparation of Sample)

1. Preparation of AFDX0116 Solution

AFDX0116 was dissolved in purified water with a buffering agent and a tonicity agent to prepare 2% AFDX0116 solution. 1 mol/L sodium hydroxide reagent solution or dilute hydrochloric acid was added to the solution to adjust the pH thereof to neutral. Also, a buffering agent and a tonicity agent were dissolved in purified water to prepare neutral vehicle. 2.5 mL and 3 mL of the vehicles were mixed with 2.5 mL and 1 mL of 2% AFDX0116 solutions, respectively, and stirred to prepare 1% and 0.5% of AFDX0116 solutions.

2. Preparation of AFDX0250 Solution

AFDX0250 was dissolved in purified water with a buffering agent and a tonicity agent to prepare 2% AFDX0250 solution. 1 mol/L sodium hydroxide reagent solution or dilute hydrochloric acid was added to the solution to adjust the pH thereof to neutral. Also, a buffering agent and a tonicity agent were dissolved in purified water to prepare neutral vehicle. 2.5 mL and 3 mL of the vehicles were mixed with 2.5 mL and 1 mL of 2% AFDX0250 solutions, respectively, and stirred to prepare 1% and 0.5% of AFDX0116 solutions.

(Evaluation Method)

Each of the prepared solutions was topically administered to the left eye of each guinea pig (the left eyes of 3 guinea pigs for each solution) in a volume of 10 μL once daily for 5 days. The pupil diameter of each guinea pig was measured before the administration on day 5 as well as 1, 2 and 4 hours after the administration to observe the pupillary light reflex. The measured pupil diameters of each guinea pig at each measurement time were averaged to obtain a value. The obtained value was defined as the average pupil diameter. Among each average pupil diameter at each measurement time, the longest diameter was defined as the maximum pupil diameter.

(Test Result)

The result is shown in Table 13.

TABLE 13

| | Concentration | Pupil diameter before administration (mm) | Maximum pupil diameter (mm) | Measurement time of maximum pupil diameter (h) | Decreased pupillary light reflex (onset cases/ evaluation cases) |
|---|---|---|---|---|---|
| vehicle | 0% | 3.4 | 3.1 | 2 | 0/3 |
| AFDX0116 | 0.5% | 2.9 | 2.9 | 2 | 0/3 |
| solution | 1% | 2.3 | 2.8 | 2 | 0/3 |
| | 2% | 2.9 | 3.4 | 2 | 1/3 |
| AFDX0250 | 0.5% | 3.3 | 2.7 | 1 | 0/3 |
| solution | 1% | 3.1 | 4.1 | 2 | 2/3 |
| | 2% | 3.5 | 3.5 | 2 | 1/3 |

As exhibited in Table 13, it was found that AFDX0116 increased the pupil diameter and decreased the pupillary light reflex in 2% solution administration group, and AFDX0250 increased the pupil diameter and decreased the pupillary light reflex in 100 solution administration group.

Comparative Example 3: Evaluation of Mydriatic Action in Atropine Solution

An atropine solution was repeatedly topically administered to one eye of a guinea pig to evaluate the effect of the solution on mydriasis.

(Preparation of Sample)

Atropine sulfate hydrate and glycerin were dissolved in water for injection to prepare 0.001%, 0.0003% and 0.0001% atropine solutions without adjusting the pH.

(Evaluation Method)

Each of the prepared solutions was topically administered to the left eye of guinea pigs (the left eyes of 3 guinea pigs for each solution) in a volume of 10 μL once daily for 5 days. The pupil diameter of each guinea pig was measured before the administration on day 5 as well as 1, 2 and 4 hours after the administration to observe the pupillary light reflex. The measured pupil diameters of each guinea pig at each measurement time were averaged to obtain the average value. The obtained average value was defined as the average pupil diameter. Among each average pupil diameter at each measurement time, the longest diameter was defined as the maximum pupil diameter.

(Test Result)

The result is shown in Table 14.

TABLE 14

| | Concentration | Pupil diameter before administration (mm) | Maximum pupil diameter (mm) | Measurement time of maximum pupil diameter (h) | Decreased pupillary light reflex (onset cases/ evaluation cases) |
|---|---|---|---|---|---|
| vehicle | 0% | 3.4 | 3.1 | 2 | 0/3 |
| atropine | 0.0001% | 2.3 | 2.8 | 1, 4 | 0/3 |
| solution | 0.0003% | 3.0 | 3.8 | 1 | 1/3 |
| | 0.001% | 2.6 | 4.9 | 1 | 3/3 |

As exhibited in Table 14, the increased pupil diameter and the decreased pupillary light reflex were found in 0.001% and 0.0003% atropine solution administration groups.

INDUSTRIAL APPLICABILITY

The pharmaceutical composition of the present invention is effective for treating myopia, preventing myopia and/or suppressing myopia progression because (+)-11-[2-[2-[(diethylamino)methyl]-1-piperidinyl]acetyl]-5,11-dihydro-6H-pyrido[2,3-b][1,4]benzodiazepin-6-one or a salt thereof suppresses the axial length elongation and the refractive error. In addition, (+)-11-[2-[2-[(diethylamino)methyl]-1-piperidinyl]acetyl]-5,11-dihydro-6H-pyrido[2,3-b][1,4]benzodiazepin-6-one does not substantially have mydriatic action and has a higher margin of safety, and thus the pharmaceutical composition of the present invention is expected to be used as an agent for treating myopia which is superior in safety and sense of use.

The invention claimed is:

1. A pharmaceutical composition for treating myopia and/or suppressing myopia progression, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

2. The pharmaceutical composition of claim 1 which is free of (−)-11-[2-[2-[(diethylamino)methyl]-1-piperidinyl]acetyl]-5,11-dihydro-6H-pyrido[2,3-b][1,4]benzodiazepin-6-one or a salt thereof.

3. The pharmaceutical composition of claim 1 which does not substantially have mydriatic action.

4. The pharmaceutical composition of claim 1, wherein the myopia is axial myopia, refractive myopia, pseudomyopia, pathological myopia, simple myopia, extreme myopia, severe myopia, high myopia, moderate myopia, low myopia, myopia complicated by glaucoma, myopia at the risk of the onset of glaucoma, or myopia with high intraocular pressure.

5. The pharmaceutical composition of claim 1 for ocular topical administration.

6. The pharmaceutical composition of claim 5, wherein the ocular topical administration is ophthalmic administration, administration by an ophthalmic ointment, conjunctival sac administration, intravitreal administration, subconjunctival administration, sub-Tenon's administration, conjunctival sac injection, or application to the eyelid.

7. The pharmaceutical composition of claim 1 which is in the form of an eye drop, an eye gel, an ophthalmic ointment, or an injection.

8. The pharmaceutical composition of claim 1, wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.0001-5% (w/v).

9. The pharmaceutical composition of claim 1, wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.001-1% (w/v).

10. The pharmaceutical composition of claim 1, wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.001% (w/v) or more and less than 1% (w/v).

11. The pharmaceutical composition of claim 1, wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.002-0.5% (w/v).

12. The pharmaceutical composition of claim 1, wherein the concentration of (+)-11-[2-[2-[(diethylamino)methyl]-1-piperidinyl]acetyl]-5,11-dihydro-6H-pyrido[2,3-b][1,4]benzodiazepin-6-one or a salt thereof is 0.002-0.01% (w/v).

13. The pharmaceutical composition of claim 1, wherein the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof is less than 0.1% (w/v).

14. The pharmaceutical composition of claim 1, wherein the concentration of (−)-11-[2-[2-[(diethylamino)methyl]-1-piperidinyl]acetyl]-5,11-dihydro-6H-pyrido[2,3-b][1,4]benzodiazepin-6-one or a salt thereof is 0.05 part by weight or less per part by weight of (+)-11-[2-[2-[(diethylamino)methyl]-1-piperidinyl]acetyl]-5,11-dihydro-6H-pyrido[2,3-b][1,4]benzodiazepin-6-one or a salt thereof.

15. A pharmaceutical composition for suppressing the axial length elongation, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

16. A pharmaceutical composition for suppressing the refractive error, comprising (+)-11-[2-[2-[(diethylamino)methyl]-1-piperidinyl]acetyl]-5,11-dihydro-6H-pyrido[2,3-b][1,4]benzodiazepin-6-one or a salt thereof as an active ingredient, wherein the pharmaceutical composition is substantially free of (−)-11-[2-[2-[(diethylamino)methyl]-1-piperidinyl]acetyl]-5,11-dihydro-6H-pyrido[2,3-b][1,4]benzodiazepin-6-one or a salt thereof.

* * * * *